(12) United States Patent
Kovi et al.

(10) Patent No.: US 10,392,417 B2
(45) Date of Patent: Aug. 27, 2019

(54) POLYMORPH OF REGADENOSON AND PROCESS FOR PREPARATION THEREOF

(71) Applicant: Apicore US LLC, Somerset, NJ (US)

(72) Inventors: Ravishanker Kovi, Monroe, NJ (US); Jayaraman Kannapan, Gujarat (IN); Ananda Babu Thirunavakarasu, Gujarat (IN); Piyush D. Fadadu, Gujarat (IN); Piyush B. Thumar, Gujarat (IN)

(73) Assignee: Apicore US LLC, Somerset, NJ (US)

( * ) Notice: Subject to any disclaimer, the term of this patent is extended or adjusted under 35 U.S.C. 154(b) by 0 days.

(21) Appl. No.: 15/797,498

(22) Filed: Oct. 30, 2017

(65) Prior Publication Data

US 2018/0127452 A1    May 10, 2018

(30) Foreign Application Priority Data

Nov. 4, 2016  (IN) .............................. 201621037803

(51) Int. Cl.
*C07H 19/16* (2006.01)

(52) U.S. Cl.
CPC .......... *C07H 19/16* (2013.01); *C07B 2200/13* (2013.01)

(58) Field of Classification Search
None
See application file for complete search history.

(56) References Cited

U.S. PATENT DOCUMENTS

| 2,500,329 A | 3/1950 | Steitz, Jr. |
| 2014/0213539 A1 | 7/2014 | Zablocki et al. |
| 2016/0244474 A1 | 8/2016 | Kovi et al. |

FOREIGN PATENT DOCUMENTS

| WO | WO-2008143667 A1 * | 11/2008 | ........... C07H 19/167 |
| WO | 2014167046 A1 | 10/2014 | |

OTHER PUBLICATIONS

He, X., et al. Controlled Crystallization and Granulation of Nanoscale beta-Ni(OH)2 Cathode Materials for High Power Ni-MH Batteries. Journal of Power Sources, Elsevier B.V., vol. 152, 2005, pp. 285-290.

Thannhauser, S.J., et. al. Studies of Acetal Phospholipids of Brain. The Journal of Biological Chemistry, ASBMB Publications, vol. 188, Jan 1, 2051, pp. 417-421.

* cited by examiner

*Primary Examiner* — Layla D Berry

(57) ABSTRACT

Processes are provided for the preparation of a stable polymorphic form C of regadenoson, the process involving steps of a) obtaining a solution of regadenoson in benzyl alcohol solvent, b) maintaining the reaction mixture of step a) to about 10° C. to about 90° C., and c) isolating the stable polymorphic form C of regadenoson. Polymorphic form C may be characterized by an x-ray powder diffraction pattern with peaks at about 6.1, 10.2, 10.6, 19.0 and 25.4.±0.2 degrees 2-theta.

4 Claims, 2 Drawing Sheets

POLYMORPH OF REGADENOSON AND PROCESS FOR PREPARATION THEREOF

CROSS-REFERENCE TO RELATED APPLICATIONS

This non-provisional application claims the benefit of priority of Indian Patent Application No. 201621037803, filed on Nov. 4, 2016, the entirety of which is incorporated herein by reference.

FIELD OF INVENTION

The present invention provides the process for the preparation of Regadenoson and stable polymorphic form C thereof. Specifically, the present invention relates to the novel stable crystalline form of Regadenoson and the process for the preparing such polymorph.

BACKGROUND OF THE INVENTION

Regadenoson is an $A_2A$ adenosine receptor agonist that is a coronary vasodilator. Regadenoson is chemically described as adenosine, 2-[4[(methylamino)carbonyl]-1H-pyrazol-1-yl]-, monohydrate. The molecular formula for Regadenoson is $C_{15}H_{18}N_8O_5 \cdot H_2O$ and its molecular weight is 408.37.

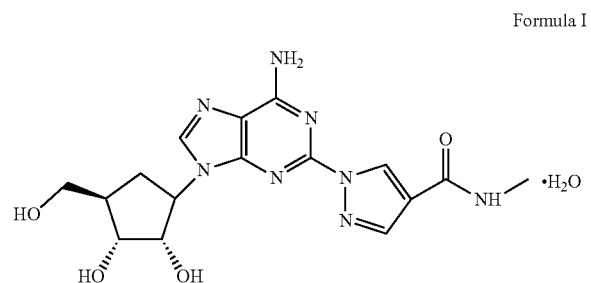

Formula I

Regadenoson approved by USFDA and is marketed by Astellas pharma under the tradename Lexiscan®. Lexiscan is a sterile, nonpyrogenic solution for intravenous injection.

Regadenoson was first described in U.S. Pat. No. 6,403,567 describes the process for the preparation of Regadenoson.

U.S. Pat. No. 8,106,183 describes monohydrate crystalline form of Regadenoson, and the process for the preparation of the same and its pharmaceutical composition.

International application number WO 2008143667 describes polymorphic form A, form B and form C of Regadenoson. Form A is stable and monohydrate form while form C is unstable.

WO2014167046 describes various polymorphic forms of Regadenoson designated as trifluroethanol (form E), ethanol (form F) and anhydrous (form G), and its process for the preparation of the same.

U.S. Pat. No. 9,441,006 describes polymorphic form E and its process for the preparation of the same.

WO2014207758 describes the propylene glycol solvate and its process for the preparation of the same.

International application number WO 2017042837 describes the crystalline form S of Regadenoson and process for the preparation of the same.

Indian application IN 1470/MUM/2011 describes the polymorphic form D, form E, form F, and form G, process for the preparation of same and pharmaceutical composition of same.

The discovery of new polymorphic forms and/or solvates of a drug or a pharmaceutically useful compound provide opportunity to improve the characteristics of a pharmaceutically acceptable dosage form of the drug with a targeted release profile or other desired characteristics.

Despite the disclosures mentioning various polymorphic forms, there is a need for new polymorphic form of Regadenoson and process for preparation thereof.

SUMMARY OF THE INVENTION

In an embodiment, the present disclosure discloses novel process for the preparation of stable Regadenoson polymorphic Form C thereof. Compounds disclosed herein may be used as coronary vasodilators as well as therapeutics for any other disorders mediated by $A_2A$ receptors.

In one embodiment, the present invention relates to a process for the preparation of Regadenoson, in high purity and high yield by using 2-chloro adenosine as starting material.

In current aspect of the present embodiment, encompasses condensation of 2-chloro adenosine namely formula VI

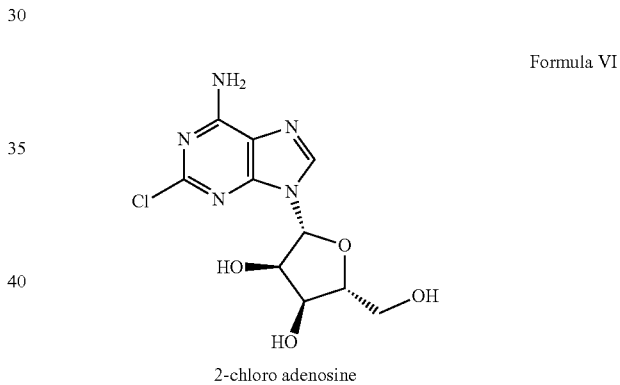

Formula VI 2-chloro adenosine with hydrazine hydrate in suitable solvent to give 2-hydrazine adenosine namely formula V.

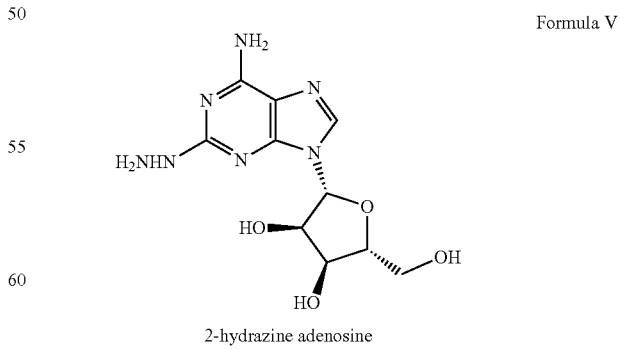

Formula V 2-hydrazine adenosine

In another aspect of the present embodiment, encompasses a process for the preparation of pyrazolo ester namely formula III

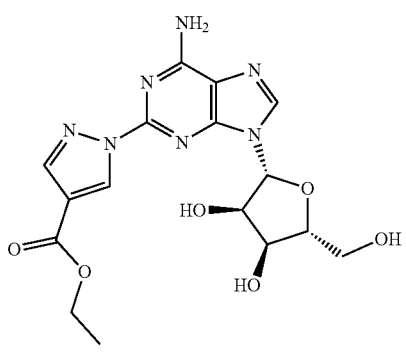

Pyrazolo ester
Formula III by reacting 2-hydrazine adenosine namely formula V

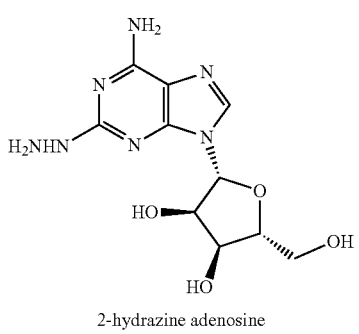

2-hydrazine adenosine
Formula V with (Ethoxy carbonyl) malondialdehyde namely formula IV in suitable solvent.

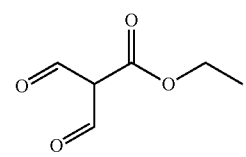

(Ethoxy carbonyl) malondialdehyde
Formula IV

In another aspect of the present embodiment, encompasses a process for the preparation of 1-(6-amino-9-((2R,3R,4S,5R)-3,4-dihydroxy-5-(hydroxymethyl)tetra hydrofuran-2-yl)-9H-purin-2-yl)-N-methyl-1H-pyrazole-4-carboxamide (Regadenoson Technical) namely formula II,

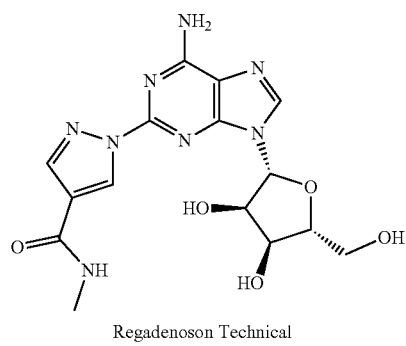

Regadenoson Technical
Formula II by reacting pyrazolo ester namely formula III in aqueous methylamine solution.

In another embodiment, present application provides stable crystalline form of Regadenoson Form C and processes for their preparation thereof.

In same aspect of present embodiment, a process for the preparation of form C of 1-(6-amino-9-((2R,3R,4S,5R)-3,4-dihydroxy-5-(hydroxymethyl)tetra hydrofuran-2-yl)-9H-purin-2-yl)-N-methyl-1H-pyrazole-4-carboxamide (Regadenoson-API) namely formula I

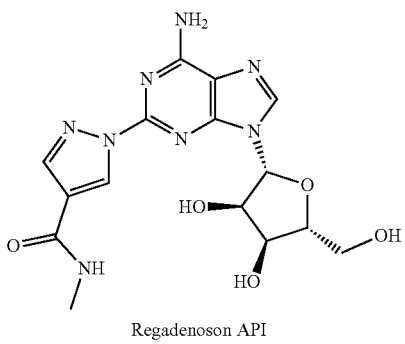

Regadenoson API
Formula I by treating Regadenoson technical with benzyl alcohol.

In an another embodiment, the present application provides crystalline Regadenoson, Form C and process for the preparation of same, form C is characterized by data selected from the group consisting of: an x-ray powder diffraction pattern with peaks at about 6.1, 10.2, 10.6, 19.0 and 25.4.±0.2 degrees 2-theta; an x-ray powder diffraction pattern with peaks at about 14.1, 18.2, 17.7, 22.6, 24.7±0.2 degrees 2-theta; an x-ray powder diffraction pattern substantially as depicted in FIG. 1; and combination thereof.

In another embodiment, the present application encompasses a process for preparing Regadenoson form C comprising the steps of:
a) obtaining a solution of Regadenoson in benzyl alcohol solvent;
b) maintaining the reaction mixture of a) to about 10° C. to about 90° C.;
c) isolating the Regadenoson form C.

DETAILED DESCRIPTION OF THE INVENTION

The present application provides process for the preparation of Regadenoson and crystalline forms preparation of Regadenoson designated as Form C.

In one embodiment, the present invention relates to a process for the preparation of Regadenoson, in high purity and high yield by using 2-chloro adenosine as starting material.

The synthesis of Regadenoson is performed as shown in Reaction Scheme I.

Reaction Scheme 1

Reaction Scheme 1

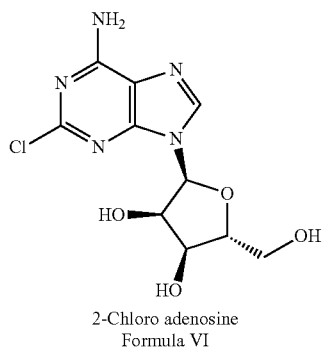

2-Chloro adenosine
Formula VI

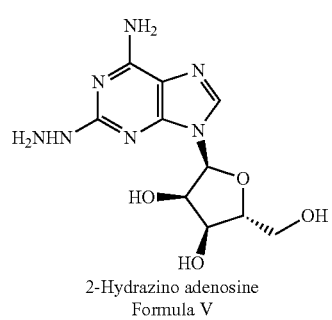 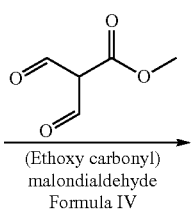

2-Hydrazino adenosine
Formula V (Ethoxy carbonyl) malondialdehyde
Formula IV

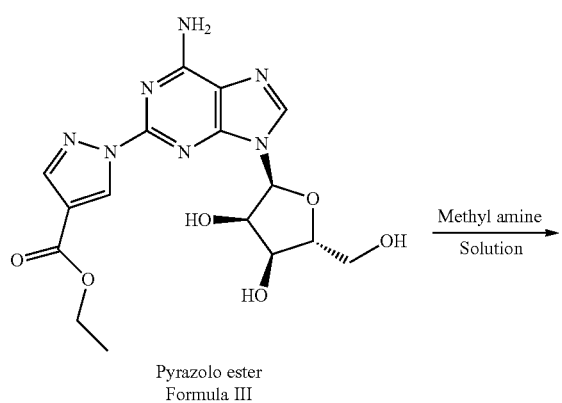

Pyrazolo ester
Formula III

Methyl amine Solution

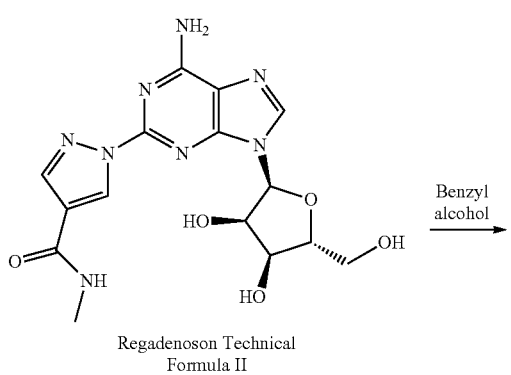

Regadenoson Technical
Formula II

Benzyl alcohol

-continued

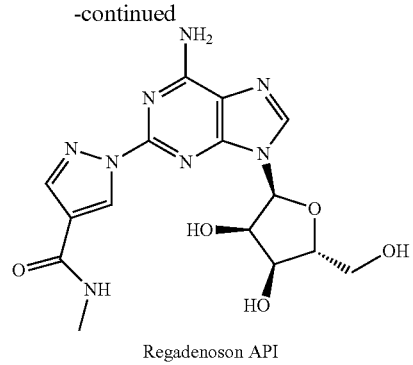

Regadenoson API
Formula I

In current aspect of the present embodiment, encompasses condensation of 2-chloro adenosine namely formula VI

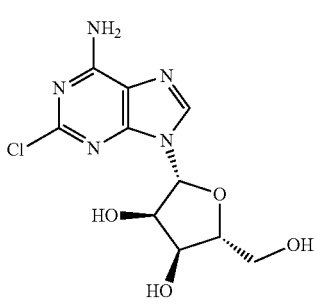

Formula VI 2-chloro adenosine with hydrazine hydrate in suitable solvent to give 2-hydrazine adenosine namely formula V.

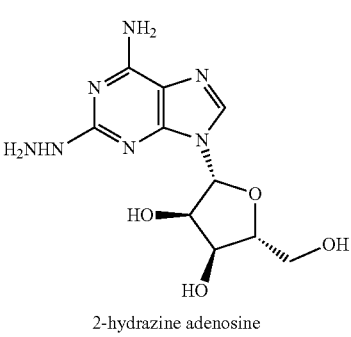

Formula V 2-hydrazine adenosine

In one embodiment this reaction is performed in 60-90% solution of hydrazine hydrate for such an example 80%. In further embodiments, the reaction is conducted at a temperature of between about 30° C. and about 70° C., for example between about 40° C. and about 60° C., such as at about 50-55° C. In additional embodiments, the reaction proceeds for between about 1 hours and about 4 hours, such as between about 2 and about 3 hours.

In certain embodiments, the reaction is conducted in a polar solvent. For example, the solvent may be an organic solvent, such as acetonitrile, water, dimethyl sulfoxide, dimethyl formamide, dichloroethane, dichloromethane, methanol, ethanol, and mixtures thereof. For particular embodiment, the solvent is water In another aspect of the present embodiment, encompasses a process for the preparation of pyrazolo ester namely formula III

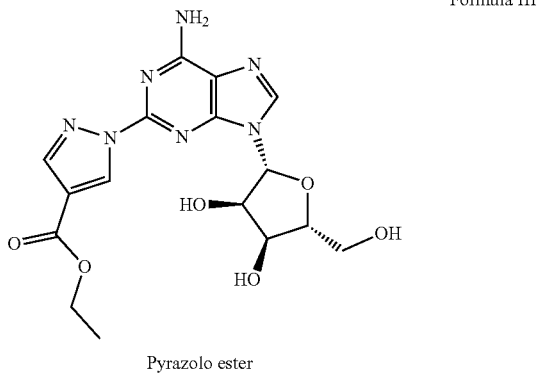

Pyrazolo ester by reacting 2-hydrazine adenosine namely formula V with (Ethoxy carbonyl) malondialdehyde namely formula IV in suitable solvent.

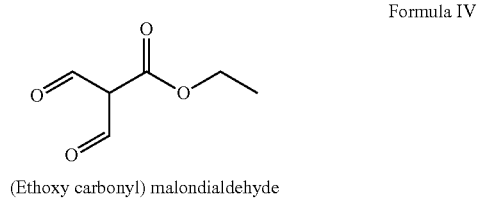

(Ethoxy carbonyl) malondialdehyde

In one embodiment, the reaction is performed using at about 0.5 eq. to about 3.0 eq., more preferably at about 1.0-2.0 eq., more preferably 1.2 eq. of (Ethoxy carbonyl) malondialdehyde namely formula IV with solvent preferably water at 60-65° C.

In another aspect of the present embodiment, encompasses a process for the preparation of 1-(6-amino-9-((2R, 3R,4S,5R)-3,4-dihydroxy-5-(hydroxymethyl)tetra hydrofuran-2-yl)-9H-purin-2-yl)-N-methyl-1H-pyrazole-4-carboxamide (Regadenoson Technical) namely formula II,

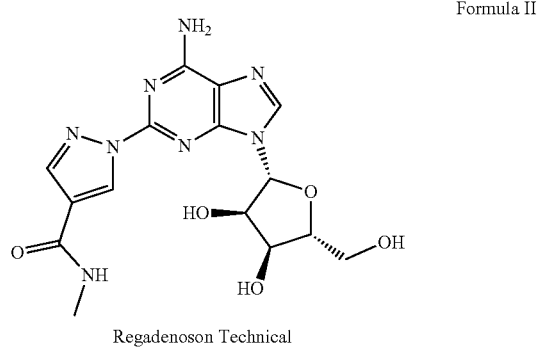 [SMILES: CNC(=O)c1cnn(-c2nc(N)c3ncn([C@@H]4O[C@H](CO)[C@@H](O)[C@H]4O)c3n2)c1]

Regadenoson Technical by reacting pyrazolo ester namely formula III in aqueous methylamine solution. In one embodiment the reaction is conducted in an aqueous solution of methylamine, initially at a temperature of about 0 to −20° C., more preferably at −5° C. to −10° C., followed by warming to about 30° C. to about 50° C., more preferably about 35-40° C.

Figure 1:
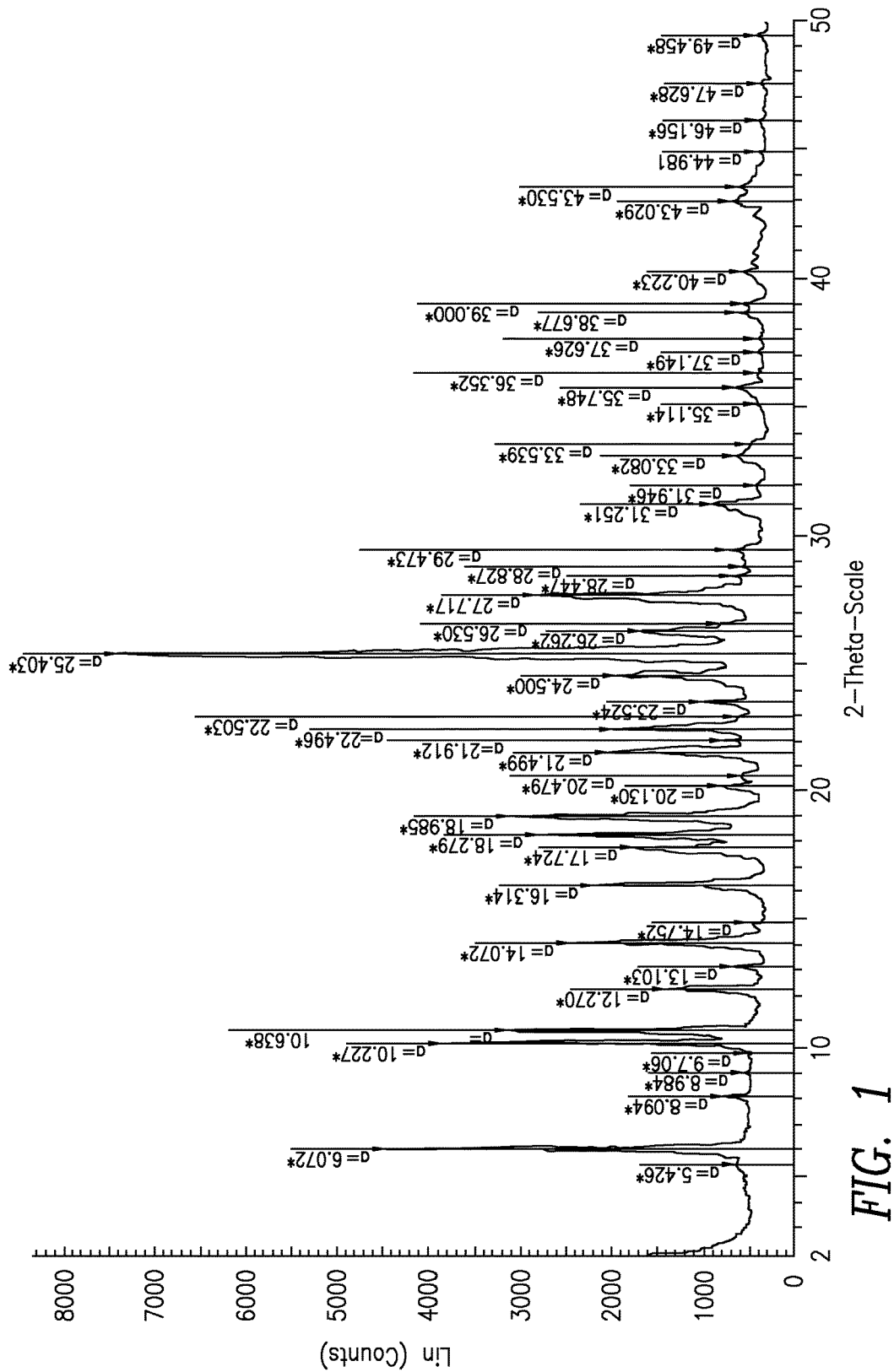
FIG. 1 illustrative a characteristic X-ray powder diffraction pattern of Regadenoson form C.
Figure 2:
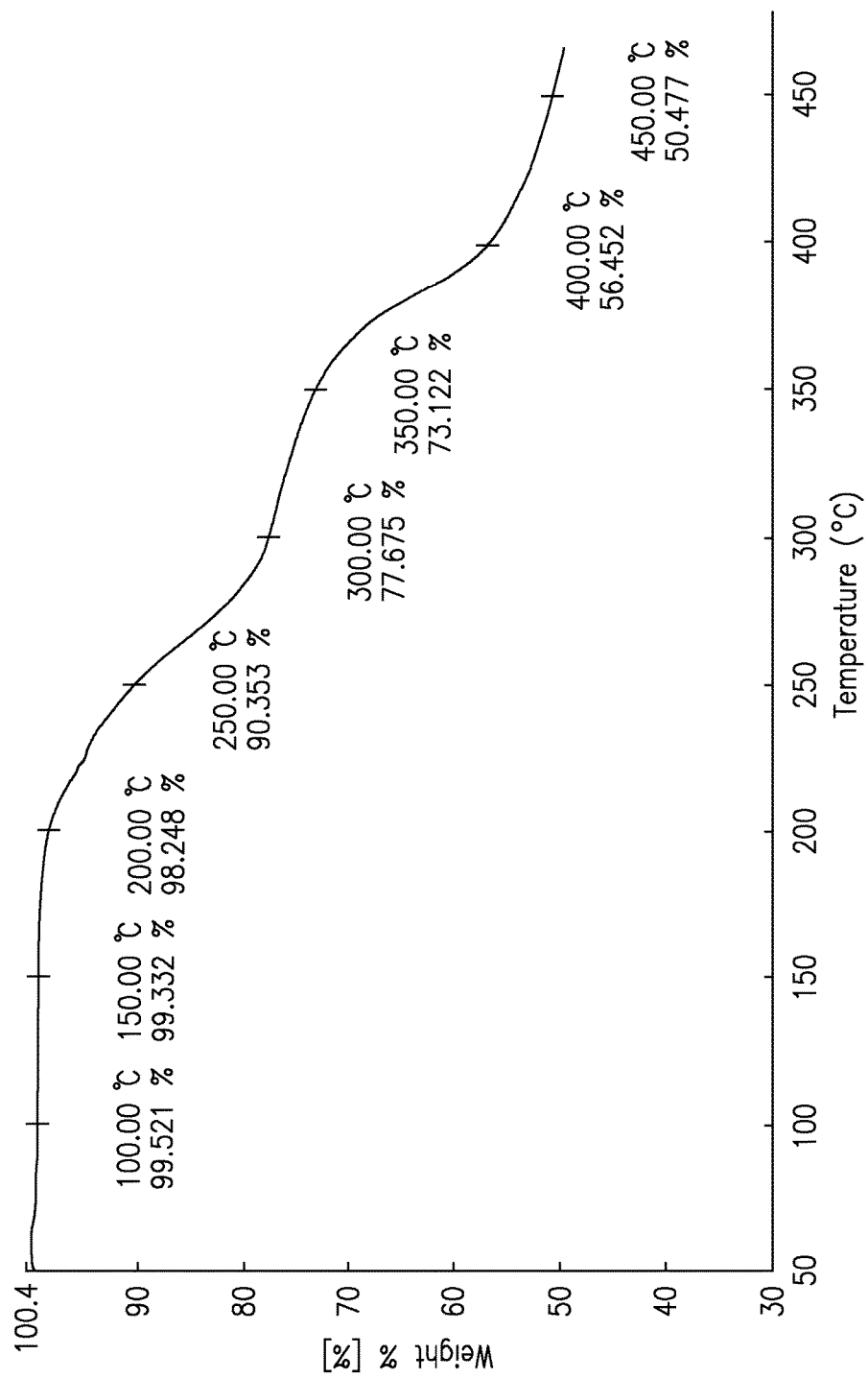
FIG. 2 illustrative a characteristic TGA pattern of Regadenoson form C.

In another embodiment, the present invention provides crystalline Regadenoson, designated as Form C and process for the preparation of thereof. Polymorphic form C is characterized by data selected from the group consisting of: an x-ray powder diffraction pattern with peaks at about 6.1, 10.2, 10.6, 19.0 and 25.4.±0.2 degrees 2-theta; an x-ray powder diffraction pattern with peaks at about 14.1, 18.2, 17.7, 22.6, 24.7±0.2 degrees 2-theta; an x-ray powder diffraction pattern substantially as depicted in FIG. 1; and combination thereof.

In another embodiment, the present application encompasses a process for preparing Regadenoson form C comprising the following steps:

a) obtaining a solution of Regadenoson in benzyl alcohol solvent;

b) maintaining the reaction mixture of a) to about 10° C. to about 90° C.;

c) isolating the Regadenoson form C.

Step a) involves obtaining a solution of Regadenoson in benzyl alcohol solvent. Obtaining a solution according to step a) includes dissolving Regadenoson in benzyl alcohol solvent or obtaining a solution of Regadenoson in benzyl alcohol as a final step in the preparation of the compound.

Step b) involves optionally heating the solution of step a) at any temperature ranging from about 0° C. to about reflux temperature of the solvent, preferably at about 50° C. to about 100° C., more preferably at about 70° C. to about 75° C. The solution may be stirred at same temperature in this case at about 70° C. to about 75° C. for 30 minutes to 4 hours, more preferably 1 hour to 3 hours, more preferably for 2 hours.

Step c) involves maintaining the reaction mixture of step b) at a temperature of about 0° C. to about 50° C. The reaction mixture of step c) is maintained at a temperature of about of about 0° C. to about 50° C. for sufficient time. Sufficient time as disclosed herein is the time required to ensure the formation of crystalline Regadenoson. In an embodiment, the reaction mixture is maintained for a time period of about 30 minutes to about 50 hours. In an embodiment, the reaction mixture is maintained at a temperature of about 10° C. to about 40° C., more preferably at about 25° C. to about 30° C.

Step d) involves isolating Regadenoson form C. The crystalline Regadenoson form C is isolated in a manner known per se, and depending on the solvent used, which include, but not limited to filtration by gravity or by suction/vacuum, distillation, centrifugation, or slow evaporation or the like. In an embodiment, Regadenoson Form C may be isolated by filtration under vacuum and suction drying at a temperature of about 25° C. to about 30° C.

Drying the crystalline Regadenoson form C may be suitably carried out using any equipment such as a gravity oven, tray dryer, vacuum oven, Büchi® Rotavapor®, air tray dryer, fluidized bed dryer, spin flash dryer, flash dryer, and the like. In an embodiment, the drying may be carried out at atmospheric pressure or under reduced pressures. In an embodiment, the drying may be carried out at a temperature of about 30° C. to about 70° C., at a temperature of 40° C. to about 60° C., more preferably at a temperature of about 45° C. to about 50° C. The drying may be carried out for any time periods required for obtaining a desired quality, such as from about 15 minutes to several hours, or longer, more preferably for 36 hours in this case.

The crystalline form of Regadenoson designated as form C of the present invention have advantageous properties selected from at least one: chemical purity, stability—such as storage stability, stability to dehydrate, stability to polymorphic conversion, flowability, solubility, morphology or crystal habit, low hygroscopicity, yield and low content of residual solvents.

Certain specific aspects and embodiments of the present application will be explained in more detail with reference to the following examples, which are provided only for purposes of illustration and should not be construed as limiting the scope of the present application in any manner.

EXAMPLES

Example 1: Preparation of 2-Hydrazino Adenosine from 2-Chloro Adenosine

Hydrazine hydrate (80% in water) solution (500.00 mL) was heated at 50° C.-55° C. and charged 2-chloroadenosine (100.00 gm) at 50° C.-55° C. in one lot. Heated reaction mass at 50° C.-65° C. for 2 hours (until 2-chloro adenosine consumed completely) and reaction mass monitored by HPLC. Distil out the reaction mass completely under vacuum at 70-75° C. and then charge process water (200 ml), again distil out reaction mass under vacuum at 70-75° C. followed by degassing. Charge process water in degassed material and then stirred reaction mass at 55-60° for 30 minutes. Cooled the reaction mass at 25-30° C. and stir for 1 hour. Filtered the reaction mass and washed with process water (100.00 mL×3), Suck dried well. Dried at 45-50° C. Dry Weight: 70.00-85.00 gm Example 2: Preparation of Pyrazolo Ester from 2-Hydrazino Adenosine 2-hydrazino adenosine (100.00 gm), process water (4000.00 mL) and (ethoxy carbonyl) malondialdehyde (72.73 gm) was taken and stirred. Reaction mass was heated at 60-65° C. and stirred for 4 hours. Cooled the reaction mass to get 25-30° C. and stirred for 1 hour. Filtered the reaction mass and washed with process water (100.00 mL×3). Suck dried well. Dried at 50-55° C. Dry Weight: 130.00 gm-136.00 gm Example 3: Preparation of Regadenoson Technical from Pyrazolo Ester A methylamine solution (40%) was cooled to get −5° C. to −10° C. Pyrazolo ester (100.00 gm) was added in it and stirred for 6 hours (till complies by HPLC). Raise the temperature to 35-40° C. and then distilled out reaction mass under vacuum below 40° C. Reaction mass cooled to 25-30° C. and stirred for 1 hour. Filtered the reaction mass and washed by process water (100.00 mL×3). Suck dried well.

Example 4: Purification of Regadenoson Technical in Acetone and N,N-Dimethyl Formamide Wet cake was taken in acetone (1400 ml) and stirred for 3 hours at 20-30° C. Filter the reaction mass and wash by acetone (100 mL), suck dried well. Wet cake was taken in N,N-dimethyl formamide (1105 ml) and reaction mass heated to get clear solution. Charcoal treatment was carried out. Clear reaction solution was taken and heated to get 45-50° C. Acetone (1275 ml) was added in above reaction mass at 45-50° C. and further maintained at same temperature for 15 hours. Filtered the reaction mass, suck dried well and wash with N,N-Dimethylformamide: acetone Mixture (50 mL: 50 mL) (50 mL×2). Again solid washed by acetone (85 mL×2). Wet cake was taken in acetone (600 ml) and stirred for 2 hours at 20-25° C. 34. Filtered the reaction mass and washed with acetone (50 mL). Suck dried well. Wet cake was taken in toluene (1200 ml) and reaction mixture was refluxed azeotropically. After completion of it reaction mass was cooled to 25-30° C. Reaction mass filtered and washed with toluene (100 ml). Suck dried well and dried at 50-55° C. Dry Weight: 55 gm-60 gm.

Example 5: Preparation of Regadenoson Form C from Regadenoson Technical

Regadenoson of Example 4 (100.00 gm) and benzyl alcohol (3000.00 mL) were heated at 70-75° C. and maintained for 2 hours. Reaction mass cooled to 25-30° C. and further maintained for 3 hours. Filtered the reaction mass and washed with benzyl alcohol (100.00 mL) Suck dried well. Dried at 50-55° C. under vacuum. Dry Weight: 80.00 gm-90.00 gm

We claim:

1. A process for the preparation of stable polymorphic form C of regadenoson, comprising the steps of:
    a) obtaining a solution of Regadenoson in benzyl alcohol solvent;
    b) maintaining the reaction mixture of step a) to about 10° C. to about 90° C.; and
    c) isolating the stable polymorphic form C of regadenoson.

2. The process of claim 1, wherein in step b), the mixture is heated to a temperature from about 70° C. to about 75° C.

3. The process of claim 1, wherein in step c), the mixture is cooled to a temperature of about 25° C. to about 30° C.

4. The process of claim 1, wherein the obtained stable polymorph form C has purity greater than 99%.

* * * * *